United States Patent [19]
Mohajer

[11] Patent Number: 5,865,765
[45] Date of Patent: Feb. 2, 1999

[54] DILATOR/SAMPLER FOR SAMPLING MATERIALS AND FLUID FROM A BODY CAVITY

[76] Inventor: Reza S. Mohajer, 1565 W. Big Beaver Rd. Bldg. F, Troy, Mich. 48084

[21] Appl. No.: 543,593

[22] Filed: Oct. 16, 1995

[51] Int. Cl.[6] .................................................. A61B 10/00
[52] U.S. Cl. ............................................................ 600/570
[58] Field of Search .................................... 128/754, 755, 128/756, 757, 758

[56] References Cited

U.S. PATENT DOCUMENTS

| 2,514,665 | 7/1950 | Myller ..................................... | 128/757 |
| 3,308,825 | 3/1967 | Cruse ...................................... | 128/757 |
| 4,227,537 | 10/1980 | Suciw et al. ............................. | 128/756 |
| 5,535,756 | 7/1996 | Parasher ................................... | 600/569 |

*Primary Examiner*—Max Hindenburg
*Assistant Examiner*—Pamela L. Wingood
*Attorney, Agent, or Firm*—Marc J. Luddy

[57] ABSTRACT

A dilator/sampler for sampling materials and fluid from a body cavity, the device comprising: a shaft having a distal end, and a proximal end; a Z-shaped sampler having a first sampling surface and a second sampling surface parallel to each other joined by a diagonal connector, the first sampling surface and the second sampling surface corresponding to the parallel bars of the Z shaped sampler where the first sampling surface is attached to the distal end of the shaft; and a conical dilator having a tip and a base attached at the base to the second sampling surface. The invention also comprises a sheath having a distal edge and a proximal end surrounding the dilator/sampler. In another embodiment of the invention, the base of the conical dilator is shaped to function as a sampler.

10 Claims, 2 Drawing Sheets

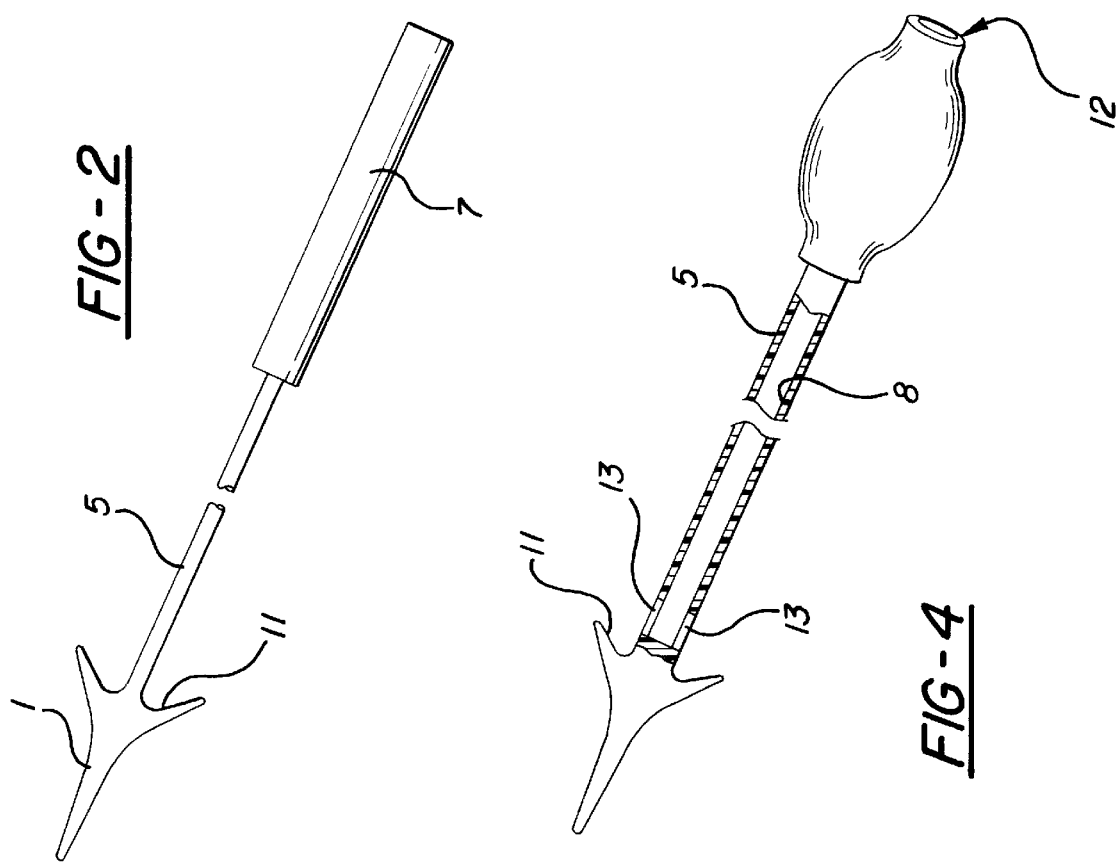
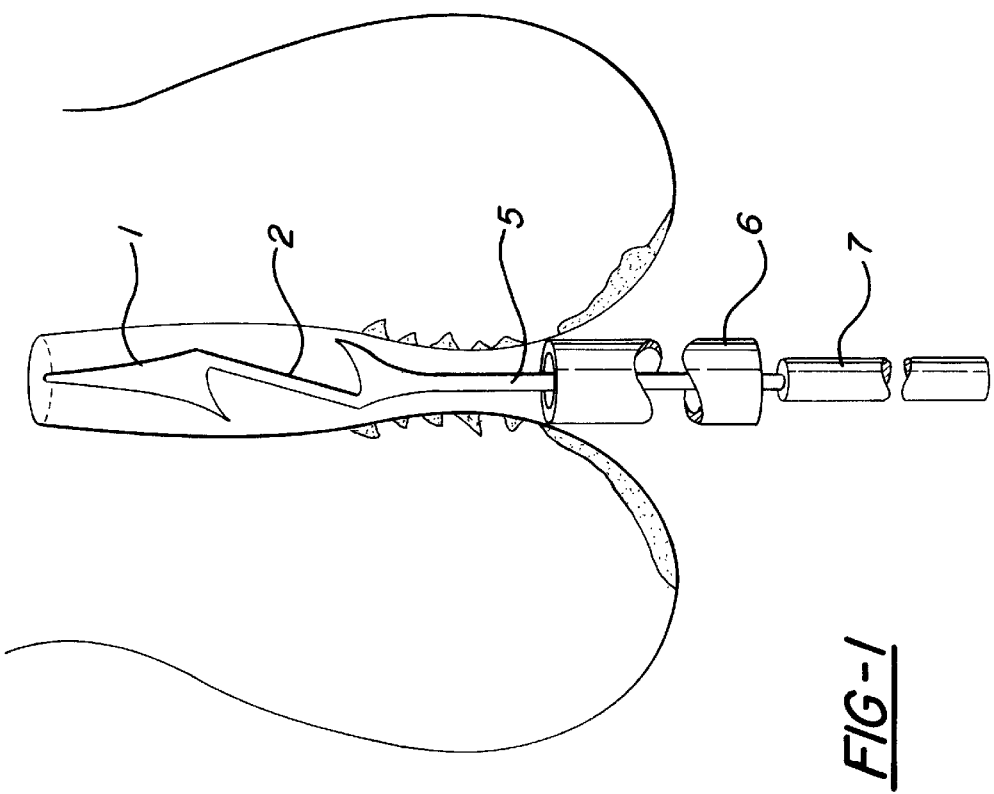

DILATOR/SAMPLER FOR SAMPLING MATERIALS AND FLUID FROM A BODY CAVITY

FIELD OF THE INVENTION

The present invention relates to a medical device that simplifies inserting the sampling device and the act of sampling tissue from body cavities, particularly the human uterus. This invention relates generally to a combined endocervical curette and endocervical scraper. This device is useful for detecting cervical cancer beyond the site of the colposcope and in all endoscopic examinations. More specifically, the present invention relates to an improved device to obtain complete tissue samples from inside the uterus without contamination. Thus assuring more accurate diagnosis of disease pathologies.

BACKGROUND OF THE INVENTION

The detection of abnormal cell growth in the cervix is important for detecting a number of disease conditions from precancerous atypical dysplasia to invasive cancer. This procedure begins by first obtaining a pap smear of the area. If the pap smear is positive, or abnormal, a physician usually examines the patient further. The physician typically uses a magnifying colposcope to identify and examine suspicious areas in the transitional zone and takes biopsies of these areas with the aid of a colposcope. Alternately, if the upper areas of the cervix at or beyond the internal os are involved, the physician will typically take a blind biopsy using a device such as a Cell Sweep® (described in detail in U.S. Pat. No. 5,002,408 and U.S. Pat. No. De 335,706 to Mohajer) and using a curette to make an endocervical curettage (ECC) around the entire area.

The cervix presents problems for the physician, particularly in the area up to the anatomical internal os. This is an area that it is difficult for the physician to observe directly even with the aid of instruments. It follows therefore that biopsy sampling and curettage is problematic. The ECC procedure is very important. Approximately 14% of lesions picked up by a pap smear occur up to the internal os area, beyond the area seen in a colposcopic examination.

Endometrial tissue sampling devices for securing and removing endometrial tissue are typically terminated at the distal end by a scraping member. Some kind of suction is usually included with the sampling device or some kind of suction probe inserted into the uterus following scraping to gather loosened tissue.

U.S. Pat. No. 3,777,643 to Binard et al, describes an endometrial sampler comprising a rigid hollow tube having a sampling end with a plurality of sampling ports communicating with the interior of the tube. Essentially, the sampler is a flexible plastic rod with a stainless steel probe that is manipulated with a syringe to gather fluid samples from the uterus. The probe does not have a cutting port.

U.S. Pat. No. 4,340,066 to Shah describes an instrument having a longitudinal chamber with a slot and a transverse slot. The handle is connected to a syringe and the physcian uses the entire probe to scrape and gather tissue samples.

U.S. Pat. No. 4,393,879 to Milgrom discloses a curette with a tissue-scraping device such as a spoon at one end. The handle member is operated by utilizing both hands to produce a sucking action to collect the tissue samples.

U.S. Pat. No. 4,396,022 to Marx describes an endometrial tissue sampling apparatus that includes a probe made of stainless steel for scraping and removing endometrial tissue. The probe is covered in a sheath. The user inserts the probe into the endometrial cavity and begins blindly scraping and cutting tissue samples. A syringe is attached to the sheath, and it is utilized to create a vacuum so the tissue samples can be sucked into the shaft and then into the syringe.

U.S. Pat. No. 4,627,444 to Booker describes a device for sampling tissues and fluids from body cavities. This device has a tube within a tube, with a retrieval line, multiple cutting edges, a protective sleeve, a stop sleeve, a plug and a cap. The catheter has integral parts and appears to be a rather difficult instrument to use. After insertion, the protective cap or tip is dislodged into the patient and the probe or curette includes a plurality of notches for blindly scraping tissue samples from the cavity walls. A syringe is attached and provides suction to collect the scraped tissue samples.

The devices described in the above references illustrate a variety of approaches to retrieving endometrial tissue samples. However, all of these devices are relatively complicated and fall short of attaining the most accurate sample possible.

In addition, every cervix differs in size according to a number of factors such as age and the number of births. The insertion of prior art ECC devices typically involve dilating the cervix using a separate dilator. This procedure can vary from uncomfortable to painful. Frequently the dilator used must be larger than the ECC device because the dilator must be removed and the ECC inserted. The time involved obviously increases the period of time discomfort or pain must be endured by the patient.

For some women the pain is significant enough that they refuse an ECC despite the risk of missing an invasive cervical cancer. The results of this can be fatal. and radiation therapy or radical surgery, even if successful in stopping the cancer, can still result in loss of sexual function and fertility.

SUMMARY OF THE INVENTION

An object of the present invention is a curette for ECC that shortens the time required for an ECC and simultaneously obtains a complete tissue and mucus sample from the area of the cervix up to the internal os.

Another object of the present invention is to reduce the discomfort experienced by a patient during and ECC.

It is still another object of the present invention to provide a disposable device for ECC that can be removed from a handle and placed in toto in a jar of fixative with the biopsied material.

These and other objects are achieved by a dilator/sampler for sampling materials and fluid from a body cavity comprising: a shaft having a distal end, and a proximal end; a Z-shaped sampler having a first sampling surface and a second sampling surface parallel to each other joined by a diagonal connector, the first sampling surface and the second sampling surface corresponding to the parallel bars of the Z shaped sampler where the first sampling surface is attached to the distal end of the shaft; and a conical dilator having a tip and a base attached at the base to the second sampling surface.

Other objects are achieved by the above described medical device that further comprises a sheath having a distal edge and a proximal end surrounding the dilator/sampler.

Other objects are achieved by the above described medical device where the conical dilator seals against the distal edge of the sheath.

Still another object of the invention is satisfied by a dilator sampler evice for sampling tissue from a body cavity, the device comprising: dilator/sampler comprising a distal end, a medial portion, and a proximal end; a conical dilator having a tip and a base attached at the base to the distal end of the dilator/sampler where the base of the conical dilator is shaped to function as a sampler.

BRIEF DESCRIPTION OF THE DRAWINGS

FIG. 1 is a cross section of the dilator/sampler where the sampler is Z-shaped.

FIG. 2 is a cross section of the dilator/sampler where the sampler is formed from the base of the conical dilator.

FIG. 4 is cross section of the dilator/sampler having the sampler formed from the base of the conical dilator where the shaft is hollow to permit suction samples.

DETAILED DESCRIPTION OF THE INVENTION

Figure 5:
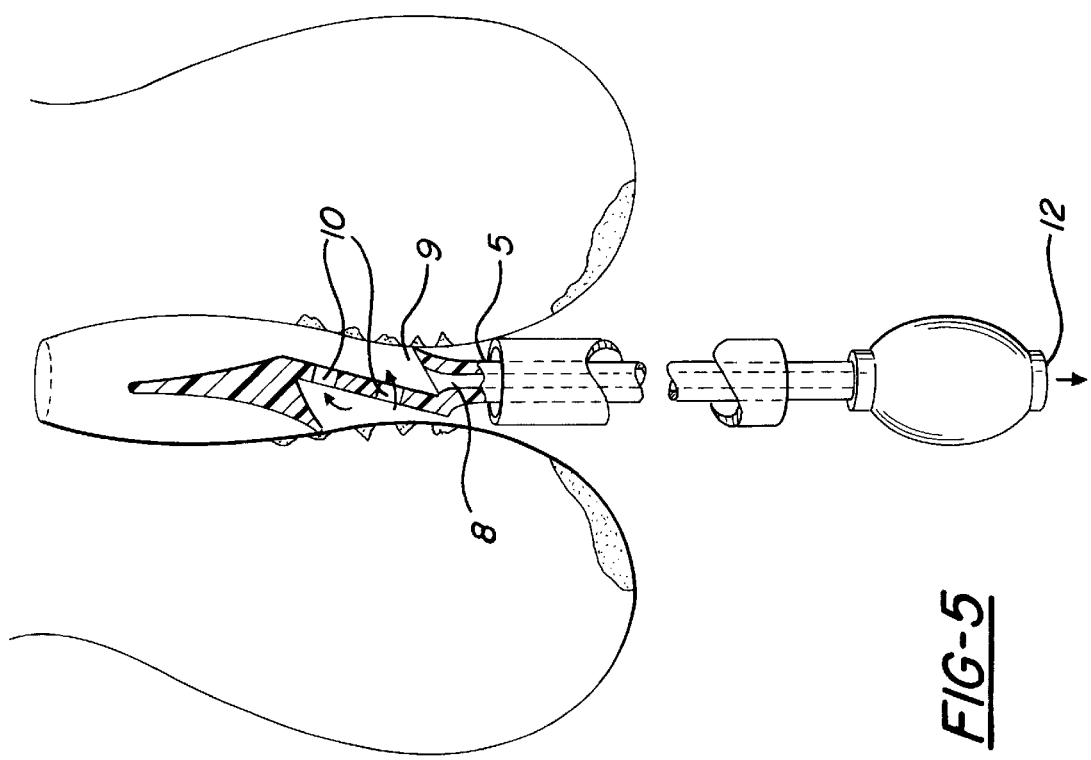
FIG. 5 is a cross section of a dilator/sampler having a Z-shaped sampler where the shaft is hollow inserted into the cervix.

The medical device for sampling tissue from a body cavity of the present invention permits a physician to do an ECC more rapidly and more completely than is possible using prior art devices. The present invention is a dilator/sampler that comprises a shaft having a distal end and a proximal end, a sampler attached to the distal end of the shaft, and a conical dilator attached to the part of the sampler farthest from the distal end of the shaft.

Referring to FIG. 1, a conical dilator 1 having a tip and a base is attached at the base to the distal end of the shaft 5. The conical dilator can be fabricated in a variety of sizes and tapers to accommodate patients of different ages and physical characteristics. Generally, the conical dilator is formed from a plastic material such as polyethylene, polypropylene, or PTFE. The conical dilator may be a straight cone, that is having the form of an equilateral triangle in cross section, or a curved cone for ease of insertion. Preferably, the conical dilator is formed from a material that is easily deformable with gentle pressure to permit the physician to provide an appropriate curve to ease its insertion into the cervix.

One aspect of the invention involves a Z-shaped sampler 2 attached between the dilator and the medial portion of said dilator/sampler. What is meant by a Z-shaped sampler is a sampler that has two cross members parallel to each other and generally perpendicular to the shaft. These cross members are joined by a diagonal connector that forms the body of the "Z" shape. The diagonally shaped area between the cross members and the diagonal connector forms two pockets where sampled material that has been scraped out of the cavity in which the sampler has been inserted can accumulate. To facilitate sampling, the tips of the cross members or sampling surfaces may be sharpened. Thus, following scraping of the cavity (cervix), the entire dilator sampler can be placed in a fixative in toto.

A preferred configuration of the invention involves enclosing the dilator/sampler in a sheath 6 having a distal edge and a proximal end. Such a sheath facilitates various aspects of insertion, use, and removal of the dilator/sampler of the invention. For example, if the base of the conical dilator 1 is configured to seal against said distal edge of the sheath, contamination of the sampler by materials outside the cavity is completely eliminated. The use of a sheath 5, also permits the withdrawal of the dilator/sampler from the proximal end of the sheath and insertion of other dilator/samplers and/or instruments, or by applying suction to the proximal end of the sheath, makes it possible to withdraw samples of materials and fluid from the cavity. It might also be desirable to apply suction to the proximal end of the sheath to remove samples of material and fluid around the dilator/sampler, that is without withdrawing the dilator/sampler from the sheath.

The handling of the sampler and its insertion and removal if desired is facilitated by the presence of a handle 7 at the proximal end of the shaft.

Figure 3:
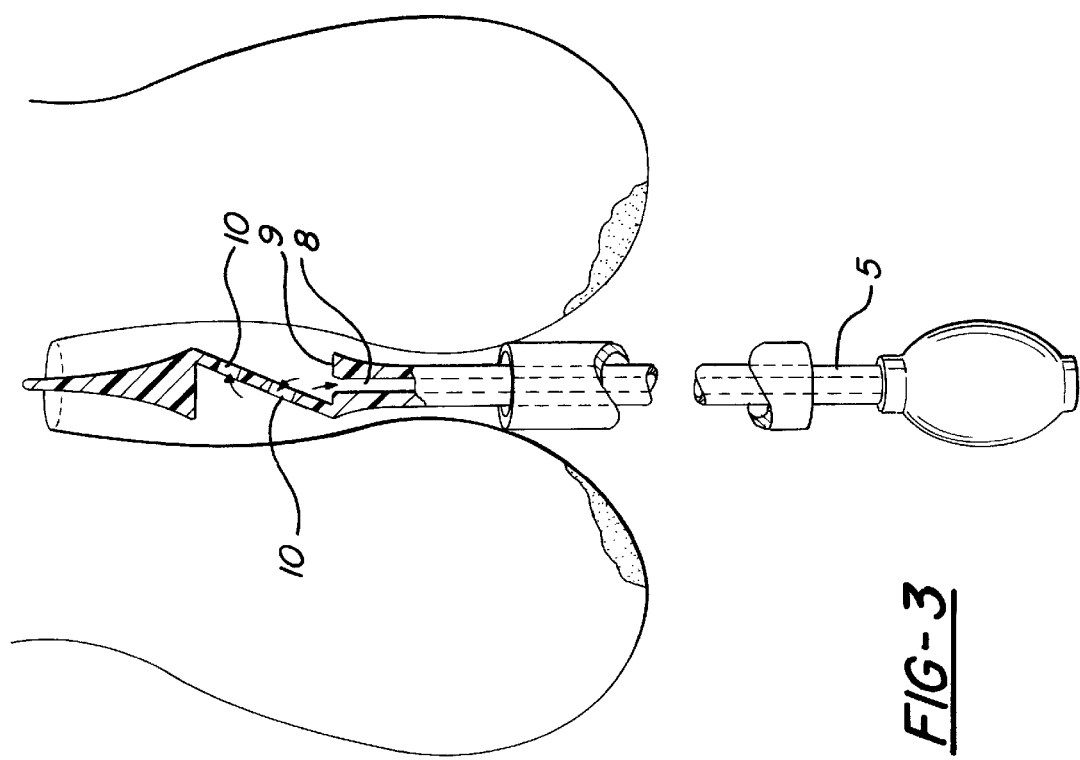
FIG. 3 is a cross section of a dilator/sampler having a Z-shaped sampler where the shaft is hollow to permit suction samples without the necessity of removing the dilator/sampler from the sheath.

In another configuration of the invention, illustrated in FIGS. 3 and 5, the shaft 5 of the dilator/sampler defines a cavity 8 open at the proximal end 12 and open at the distal end through said first sampling surface 9 and through the diagonal connector 10 to permit direct withdrawal of scraped materials and fluids using a suction device applied to the proximal end of the shaft or the sheath.

In order to judge insertion distance and make appropriate measurements, a scale may be provided at the proximal end of the shaft of the dilator/sampler to provide a reference point to determine the extent of insertion of the dilator/sampler into a body cavity.

In another configuration of the present invention, the base of the conical dilator is configured to form a sampler 11 as shown in FIGS. 2 and 4. As described above, the base of such a conical dilator can be configured to seal against the distal edge of the sheath. Similarly, the shaft 5 of the dilator/sampler defines a cavity 8 open at the proximal end 12 at a point 13 below the sampler 11 to permit direct withdrawal of scraped materials and fluids using a suction device applied to the proximal end of the shaft or the sheath.

The present invention provides a unique one step method of dilating the cervix and taking a complete tissue and mucus sample by successive scrapings using the same curette so that the total sample contains samples of all areas of potential abnormal cells. This invention assures that the pathologist will receive a sample of all suspect tissue and fluid and reduces the chance of a diagnostic error.

It is to be understood that the present invention is not limited to the embodiments described above, but encompasses any and all embodiments within the scope of the following claims.

I claim:

1. A dilator/sampler for sampling materials and fluid from a body cavity, said device comprising:

a shaft having a distal end, and a proximal end;

a Z-shaped sampler having a first sampling surface and a second sampling surface parallel to each other and joined by a diagonal connector, said first sampling surface and said second sampling surface corresponding to the parallel bars of said Z shaped sampler where said first sampling surface is attached to said distal end of said shaft; and a conical dilator having a tip and a base attached at said base to said second sampling surface.

2. The dilator/sampler of claim 1, further comprising:

a sheath having a distal edge and a proximal end surrounding said dilator/sampler.

3. The dilator/sampler of claim 1, where said base of said conical dilator seals against said distal edge of said sheath.

4. The dilator/sampler of claim 1, where said shaft of said dilator/sampler defines a cavity open at said proximal end and open at said distal end through said first sampling surface to permit withdrawal of scraped materials and fluids using a suction device.

5. The dilator/sampler of claim 4, where said diagonal connector defines openings that permit communication between the area defined by said second sampling surface and said diagonal connector and said cavity.

6. The dilator/sampler of claim 2, where said sheath is configured to permit withdrawal of said dilator/sampler from said proximal end of said sheath and insertion of other devices.

7. The dilator/sampler of claim 1, where said first sampling surface and said second sampling surface have tips that are sharpened to facilitate sampling.

8. The dilator/sampler of claim 1, where said proximal end of said dilator/sampler comprises a handle.

9. The dilator/sampler of claim 1, further comprising a scale at said proximal end of said shaft to determine the extent of insertion of said/dilator sampler into a body cavity.

10. The dilator/sampler of claim 2, where said proximal end of said sheath is configured for attachment of a suction device.

\* \* \* \* \*